(12) United States Patent
Corvo et al.

(10) Patent No.: US 6,495,834 B1
(45) Date of Patent: Dec. 17, 2002

(54) COMPACT MEDICAL IMAGER

(75) Inventors: Philip J. Corvo, Hudson, OH (US); Michael R. Mayhugh, Shaker Heights, OH (US); Scott T. Huth, Norton, OH (US); Kenneth Smolko, Medina, OH (US); Csaba M. Rozsa, Brecksville, OH (US); Robert S. Schreiner, Chagrin Falls, OH (US)

(73) Assignee: Saint-Gobain Industrial Ceramics, Inc., Worcester, MA (US)

( * ) Notice: Subject to any disclaimer, the term of this patent is extended or adjusted under 35 U.S.C. 154(b) by 0 days.

(21) Appl. No.: 09/418,903

(22) Filed: Oct. 15, 1999

Related U.S. Application Data

(60) Provisional application No. 60/107,378, filed on Nov. 6, 1998.

(51) Int. Cl.[7] .................................................. G01T 1/20
(52) U.S. Cl. .................................................... 250/363.1
(58) Field of Search ......................... 250/361 R, 363.01, 250/363.02, 363.1; 600/407

(56) References Cited

U.S. PATENT DOCUMENTS

| | | | | | |
|---|---|---|---|---|---|
| 2,779,876 | A | * | 1/1957 | Tobias et al. | 250/366 |
| 4,055,765 | A | * | 10/1977 | Gerber et al. | 250/370.09 |
| 4,125,776 | A | * | 11/1978 | Tosswill et al. | 378/149 |
| 4,782,840 | A | * | 11/1988 | Martin, Jr. et al. | 600/431 |
| 5,057,690 | A | * | 10/1991 | Morgan et al. | 250/336.1 |
| 5,286,973 | A | * | 2/1994 | Westrom et al. | 250/253 |
| 5,325,855 | A | * | 7/1994 | Daghighian et al. | 600/407 |
| 5,742,060 | A | | 4/1998 | Ashburn | 250/370.09 |
| 6,021,341 | A | * | 2/2000 | Scibilia et al. | 600/407 |

FOREIGN PATENT DOCUMENTS

| | | |
|---|---|---|
| FR | 0 490 753 A2 | 12/1991 |
| WO | WO 98/48300 | 10/1998 |

* cited by examiner

*Primary Examiner*—Constantine Hannaher
*Assistant Examiner*—Shun Lee
(74) *Attorney, Agent, or Firm*—Don W. Bulson; Volker R. Ulbrich

(57) ABSTRACT

A compact medical nuclear imaging device, which generates a medical image from gamma radiation, can be held stationary or moved to search a large area for locating a radioactive area of interest. The compact medical imaging device comprises a collimator having an array of collimating channels, a radiation collection module converting the gamma radiation to an electric signal, an electronic module for processing the electrical signal, and a display module for displaying a two-dimensional image of the radiation scene, all of which preferably are assembled together in a single, compact module of a size small enough to permit it to be held and maneuvered by a human operator.

18 Claims, 2 Drawing Sheets

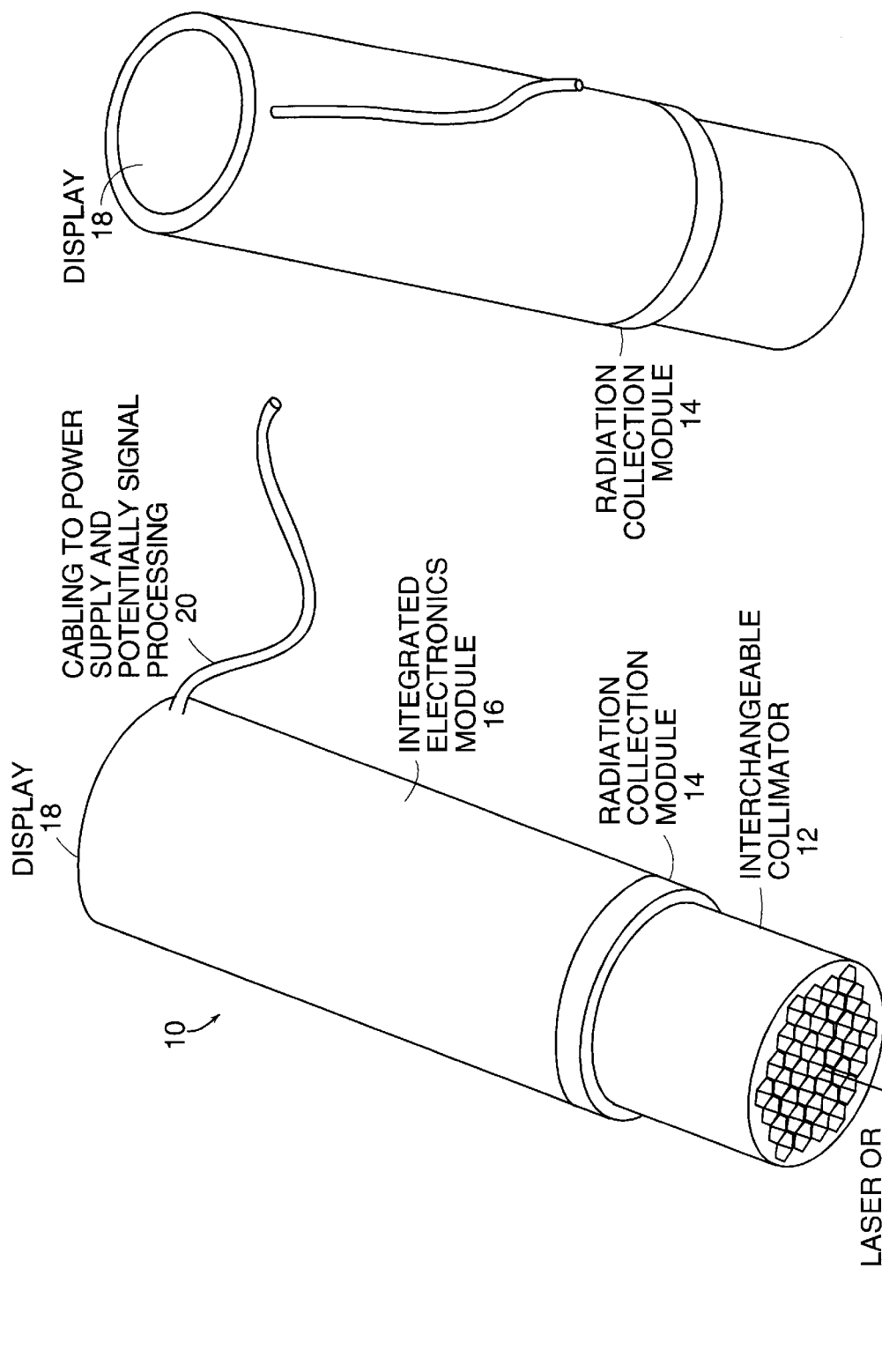

SYSTEM DIAGRAM

COMPACT MEDICAL IMAGER

This application claims the benefit of the copending provisional application No. 60/107,378 filed Nov. 6, 1998.

FIELD OF THE INVENTION

The invention relates generally to medical imaging devices and more particularly to such devices which use energy conversion devices to obtain an electrical signal in response to gamma radiation.

BACKGROUND

Medical imaging is accomplished by inducing a patient with a radiopharmaceutical substance by means of injection, swallowing, breathing, or other appropriate method. The radioactive isotope of the radiopharmaceutical migrates to the target area to be examined and results in gamma radiation from it. The radiation can be sensed and used to generate an image of some features of the target area to provide information for approprate treatment. The image is presently generated by one of various types of computer assisted tomography (CAT) systems or the like.

Sensing of radiopharmaceuticals in animals and humans is accomplished today in essentially two ways. First, large gamma cameras containing collimators and two dimensional position-sensitive radiation detectors with fields of view of 12" in diameter or more and detector heads weighing hundreds of pounds are used to make two-dimensional organ images, sometimes in a stationary mode and sometimes in a scanning mode. They are also used to make three dimensional organ images by taking several views of the same organ from different angles and using image reconstruction techniques to compute the concentration of radiopharmaceutical in three dimensions in a procedure called single photon emission tomography, or "SPECT". The objective is to image the uptake of radiopharmaceuticals in the organs or systems of interest.

In the second method a single radiation detector without imaging capability is used to locate radioactive regions by manually scanning the single detector and its collimator over the region of interest to locate "hot spots", for example indicating the presence of radiopharmaceutical tailored to be taken up by cancerous tissue. This technique is an aid in location of tissues of specific interest for which the radiopharmaceutcial is tailored, for example cancerous tissues, and specifically in some cases to aid surgeons in locating cancerous tissue and in determining if all the malignant tissue has been removed. Movement of the sensing radiation detector is essential to the technique. A 2-D (two-dimensional) or 3-D (three dimensional) image from a gamma camera might have advantages in surgery compared to the slow, cumbersome, risky method of scanning the single channel detector by moving it and it's inherently small field of view manually to locate radioactive tissue, but the massive size of the gamma camera's detector head precludes practical use in the crowded surgical theater. It's size similarly precludes practical sterilization. Accordingly, there is a need for a smaller, more portable apparatus for obtaining a medical image from the gamma radiation.

SUMMARY OF THE INVENTION

In accordance with the present invention there is provided a novel compact medical nuclear imaging device for generating a medical image from gamma radiation. It can be made small enough to be available for use in the course of surgery for making available in real time important information about the target surgery region.

BRIEF DESCRIPTION OF THE DRAWINGS

FIG. 1 is a schematic perspective view of one embodiment of an imager according to the invention, looking from the lower left.

FIG. 2 is a schematic perspective view of the imager of FIG. 1, looking from the upper right.

DETAILED DESCRIPTION

Figure 3:
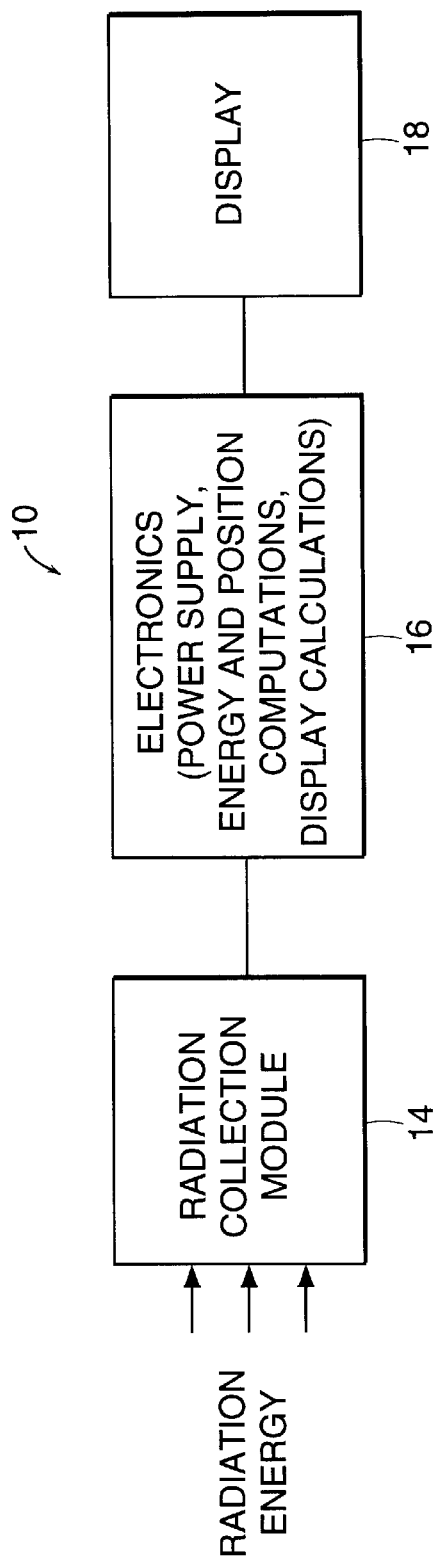
FIG. 3 is a system diagram of the imager of FIG. 1.

One embodiment of the invention is the compact medical nuclear multichannel imager 10 illustrated in FIGS. 1 and 2 and represented in flow diagram form in FIG. 3. It includes a collimator 12, a radiation collection module 14, an integrated electronics module 16, and a display module 18. The imager 10 provides full imaging capability in a stationary imaging mode and can be made in a size which permits its sterilization and use in a surgical operating room theater.

The collimator 12 may be a cylinder segment of radiation absorbing material, such as lead, with an array of mutually parallel, longitudinally extending passageways for the incident radiation.

The radiation collection module 14 may be an array of scintillation crystals, such as sodium iodide, bismuth germinate, or the like which converts the incident radiation to light in conjunction with a corresponding array of conversion devices, such as photodiodes coupled to the scintillation crystals, which further convert the light signal to an electrical signal. Alternatively, the radiation module 14 may be an array of electro-optic crystals, such as cadmium zinc telluride (CZT), which convert the incident radiation directly to an electrical signal. Each series of scintillation crystal and its associated conversion device and/or electronics constitute a single channel of the imager 10.

The integrated electronics module 16 receives the electronic signals from the channels and processes them to produce a useful image. This may be accomplished by storing the signals in an electronic memory onboard the device 10 or by sending them out in real time via the cabling 20 for further processing to generate an image on a remote monitor or on the display 18 on the back face of the imager 10. The display may be a liquid crystal or other flat panel addressed by a driver circuit which is coupled to an electronic signal processor suited for generating the image information for displaying an Anger or interpolated image. It may also be a small cathode ray tube or an array of light emitting diodes or the like.

A light emitting diode, laser, or other light beam source may be arranged to show the operator the direction of the imager by the location of its spot on the surface of the target object being surveyed. Alternatively, a plurality of laser diodes or other light emitting devices may be located at the collimator to project light on the surface of the target in the shape of a frame or raster which corresponds to the display frame, so that the operator of the imager may locate precisely the source of the image information.

In a particularly advantageous form of the imager, the integrated electronics module provides for each channel a separate output coupled to a corresponding light generating device in an array of such devices on the back face of the device 10. For example, an array of light-emitting diodes (LED's) may be the display, with each diode receiving the amplified and properly conditioned output of the channel associated with it. By "properly conditioned" is meant that the signal exceeds a predetermined threshold voltage for activating the diode and continues long enough to provide a useful visual stimulus in an image format. This would generally mean that the signal would be made longer than 1/30th of a second to prevent a flickering effect. With such an arrangement, only power is needed from outside the imager 10 via the cabling 20. However, the power could conceivably also be provided by an electrical storage battery or other power source within the housing of the imager 10.

Details of individual detector channels and the integrated electronics for each channel are within the scope of knowledge of a person skilled in the art. Examples of such channels in the context of a larger, prior art apparatus associated with computer assisted tomography are described, for example in U.S. Pat. No. 5,786,597 issued to Lingren et al and incorporated herein by reference in its entirety.

Figure 4:
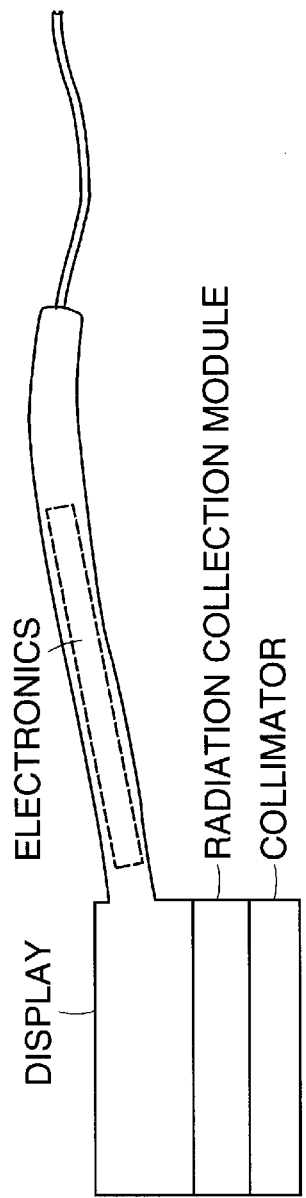
FIG. 4 is a schematic elevational view of an imager provided with a handle.

The size of the novel imager is tailored to fit the particular application desired, for example the field of interest in surgery, and to fit sterilization equipment typically available in the surgical suite. Typically the largest lateral dimension is 6" or less, and the weight no more than 50 lbs. Moreover, the imager's thickness is minimized so that including the collimator, it is 3" thick or less. Weight must be minimized for manual handling, or articulating arms may provide counterbalancing for placement. To maintain the low profile, the acquisition and image processing electronics may be remote from the detector via the cabling, so that only the collimator and channel portion sufficient to generate an electrical signal is near the patient. The signal may also travel in the cabling by optical fiber. Alternately, the imager may have electronics in a handle attached to the detector plane, either in line with the detectors, or off to the side like the handle on a spatula, as is shown in FIG. 4. In any event, the radiation sensing portion must itself often be compact, for example by using very compact photomultipliers and scintillators, or more likely photodiodes and scintillators, or semiconductor radiation detectors like cadmium zinc telluride. These techniques may provide counting through individual pixels, images through a pixel array, or images through Anger logic.

With a small, flat detector with electronics either remote or within a laterally-extending handle, the counting information or image may be displayed on the physicians side of the imager using techniques such as an LED array display or a two-dimensional flat panel display positioned to give information in a way that the radioactive tissue is located one for one to the physician. In other words, the hot spot in the patient is just below the hot spot in the image. Further, a secondary locating image may be made on a reference like a piece of film, or a plastic sheet marked with a marker, so that this reference image may be placed upon the patient after the sensing detector is removed to show the physician the location of the hot spot spatially. This secondary imaging sheet could also have a reference mark which relates to a reference mark on the detector that is transferred also to the patient.

Another way to mark the image would be to place radioactive material on the patient for short times to provide reference spots in the image. In another method, the imager and collimator can be remote enough from the patient so that the surgeons hands and instruments can be on the patient while the counting image is displayed for the surgeons review. The system must be close enough, or the collimator designed so that image resolution is still adequate for the task.

The imager has the advantage that it can be held stationary or moved to search a large area in a smaller time than is possible by scanning with an individual probe, while still locating the radioactive area of interest. Alternately, the imager can itself be moved while monitoring larger areas tracking audibly or otherwise the overall count rate or merely the count rate from the most active channel. The imaging variant of this concept has the further advantage that a record of before and after radioactivity in the surgical area can be recorded, demonstrating that the surgeon has done his task responsibly. The imager also has the advantage of being useful for searching the area of interest before surgery begins to be sure the right surgical region is opened on the first cut.

The detection process is favored by systems which reject scatter coming from the patient and surroundings and accept only full energy events emanating from the tissue under investigation. Collimation and shielding schemes are used to favor events from the subject tissue. Scatter can be further rejected by choosing detecting media that have the best energy resolution for the isotope under study. Often that detecting medium will be CZT and, more particularly, it may be CZT using single carrier selection criteria that favor accepting full energy rays over scattered ones.

What is claimed is:

1. A compact medical imaging device, comprising:

a collimator for collimating radiation emanating from a radiopharmaceutical present in a subject being examined, the collimator having an input side, an output side, a longitudinal collimation axis, and an array of collimating channels extending between the input and output sides and parallel to the collimation axis;

a radiation collection module having an input side coupled to the collimator for intercepting and converting the radiation to another energy form representative of the radiation from the output side of the collimator, thereby providing converted radiation;

an electronics module coupled to the collection module for receiving the converted radiation and generating therefrom at least one electrical signal which is representative of the radiation from the output side of the collimator;

an electrically addressable display module coupled to the electronics module for generating a two-dimensional visual display image which is representative of the radiation from the output side of the collimator; and a marking device for correlating a location in the displayed image to a location on the surface of the subject;

the collimator, radiation collection module, and display module being assembled together in a single, compact module of a size small enough to permit the compact module to be held and maneuvered by a human operator.

2. The compact imager in accordance with claim 1 wherein the radiation collection module comprises a scintillation crystal.

3. The compact imager in accordance with claim 2 wherein the electronics module comprises an array of electro-optic conversion devices for converting light from the scintillation crystal into electrical signals which are associated in at least two dimensions with the location at which the light was generated in the scintillation crystal by the radiation.

4. The compact imager in accordance with claim 3 wherein the electro-optic conversion devices are photodiodes.

5. The compact imager in accordance with claim 2 wherein the scintillation crystal is sodium iodide.

6. The compact imager in accordance with claim 1 wherein the radiation collection module comprises an electro-optic crystal for converting the radiation to an electrical signal.

7. The compact imager in accordance with claim 1 wherein the radiation collection module comprises an array of electro-optic crystals, each crystal having an input side receiving radiation from the output side of the collimator for converting the radiation to a plurality of electrical signals, each electrical signal having an amplitude which is representative of the energy of the radiation from the location of the output side of the collimator which is associated with the input of the respective crystal.

8. The compact imager in accordance with claim 7 wherein a plurality of electronic amplifying and processing signal channels are associated with and coupled to the output of a respective one of the electro-optic crystals for amplifying and processing the signal into an output signal to make it suitable for generating a visible image.

9. The compact imager in accordance with claim 8 wherein the display module comprises a two-dimensional array of electrically addressable opto-electric elements electrically coupled to and associated with the signal channels to generate from the signal outputs of the signal channels a visual image which corresponds with the radiation from the output side of the collimator.

10. The compact imager in accordance with claim 1 wherein the compact module includes a handle and the electronics module is located at least partially inside the handle.

11. The compact imager in accordance with claim 10 wherein the display module is an array of light emitting diodes, each addressed by an electronic module channel output signal.

12. The compact imager in accordance with claim 1 wherein the marking device is a light beam from the input side of the collimator.

13. The compact imager in accordance with claim 12 comprising a laser diode for generating the light beam.

14. A compact medical imaging device, comprising:

a collimator for collimating radiation emanating from a radiopharmaceutical present in a subject being examined, the collimator having an input side, an output side, a longitudinal collimation axis, and an array of collimating channels extending between the input and output sides and parallel to the collimation axis;

a radiation collection module having an input side abutting the collimator for intercepting and converting the radiation to another energy form representative of the radiation from the output side of the collimator, thereby providing converted radiation;

an electronics module coupled to the collection module for receiving the converted radiation and generating therefrom at least one amplified and processed electrical signal which is representative of the radiation from the output side of the collimator; and an electrically addressable display module coupled to the electronics module for generating a two-dimensional visual display image which is representative of the radiation from the output side of the collimator;

the collimator and radiation collection module being assembled together to form a compact module of a size small enough to permit the compact module to be held and maneuvered by a human operator, and wherein the compact module has a thickness in the direction of the collimation axis and a width transverse to the collimation axis, and the thickness is less than the width.

15. The compact imager in accordance with claim 14 wherein the compact module includes the display module in addition to the collimator and radiation collection module.

16. The compact imager in accordance with claim 14 wherein the display module is separate from the compact module and connected thereto by a cable.

17. The compact imager in accordance with claim 14 wherein the compact module includes a handle and the electronics module is located at least partly in the handle.

18. The compact imager in accordance with claim 14 wherein the compact module has a thickness no greater than 3 inches and a width no greater than 6 inches.

* * * * *